(12) United States Patent
Cardarelli (10) Patent No.: US 6,305,935 B1
(45) Date of Patent: Oct. 23, 2001

(54) DISPOSABLE CONTRA-ANGLE

(76) Inventor: Venanzio Cardarelli, 20 North Triangle Dr., Plymouth, MA (US) 02360

(*) Notice: Subject to any disclaimer, the term of this patent is extended or adjusted under 35 U.S.C. 154(b) by 0 days.

(21) Appl. No.: 09/694,924

(22) Filed: Oct. 24, 2000

Related U.S. Application Data

(60) Provisional application No. 60/163,040, filed on Nov. 2, 1999.

(51) Int. Cl.$^7$ ................................................. A61C 3/06
(52) U.S. Cl. ........................ 433/126; 433/127; 433/128
(58) Field of Search .................................... 433/115, 116, 433/127, 128, 126

(56) References Cited

U.S. PATENT DOCUMENTS

| | | | |
|---|---|---|---|
| 3,134,172 | * | 5/1964 | Sato ................................. 433/127 X |
| 5,599,184 | * | 2/1997 | Field ..................................... 433/115 |
| 5,718,582 | | 2/1998 | Quinn et al. . |
| 5,749,728 | | 5/1998 | Bailey . |
| 5,766,008 | | 6/2000 | Hughes . |
| 6,099,309 | | 8/2000 | Cardarelli . |

\* cited by examiner

*Primary Examiner*—Nicholas D. Lucchesi
(74) *Attorney, Agent, or Firm*—D. Michael Burns (57) ABSTRACT

A disposable dental contra-angle comprising a plastic housing having a sleeve, a tapered neck, a head and a disposable bur. The bur being removably coupled to a driven rotating mandrel located in the head section. The rotating mandrel having an integral axis pole member extending through and outwardly from its top and bottom portions wherein the bur is maintained in a 1:1 rotational luted connection, with virtually no slippage. The sleeve section having an elongated opening for receiving a power drive from a dental handpiece. A gear ratio mechanism located in the sleeve section rather than the head section, for either increasing or decreasing the shaft speed.

A gear to gear arrangement in the head section for translating rotation from the drive shaft to the bur. In addition to having a flat surface for a luted non-slippage connection within the rotating mandrel, the bur further has a plurality of semicircular grooves for connecting with a plurality of O-ring connections disposed within the chamber of the axis pole for prevention of axial displacement of the bur from the mandrel.

10 Claims, 6 Drawing Sheets

DISPOSABLE CONTRA-ANGLE

CROSS REFERENCE TO RELATED APPLICATION

This application is based on Provisional Patent Application Ser. No. 60/163,040 filed Nov. 2, 1999.

BACKGROUND OF THE INVENTION

My U.S. Pat. No. 6,099,309, relates generally to a disposable prophy angle. Structure of this prophy angle is utilized to contain and support the present invention.

1. Field of the Invention

The present invention relates generally to an improved disposable contra-angle. More particularly, the present invention relates to disposable burs that can be placed into rotation for high speed drive.

2. Description of the Prior Art

Dental drill burs are well known in the art. At present, they are removably placed into the contra-angle by the dentist or the dental assistant. The standard procedure is for the dentist to place the bur into the contra-angle, and after the procedure it is removed manually to be brushed and sterilized. Often, it is discarded because of wear or inability to properly clean. Because the contra-angle is subject to contamination and infection from saliva and blood of the patient, it needs to be brushed; placed into ultrasonic; sterilized; and then lubricated before it can be used again. The lubrication is very critical due to the variable speeds generated by contra-angles. Extra care must be taken to prevent any oil from escaping into the patient's mouth or on the cavity itself. Occasionally the contra-angle must be taken apart because the gears have smudge accumulation and thereby have difficulty operating. This along with normal cleaning creates a substantial time loss leading to lower productivity of the entire dental office. All of this makes the use of reasonably priced contra-angles very practical. But beyond cost, the most important reason for using disposable contra-angles is to reduce the danger from incomplete sterilization, whereby the bacteria and infection are then transferred from one patient to another.

The main problems associated with the prior art is that the retained bur has a tendency to rattle and be generally noisy. This is primarily due to the fact that they are only connected at the superior end. There definitely is too much play between the cylinder of the bur and the core of the rotating mandrel. This results in energy loss, fatigue, loss of cutting efficiency. The patients feel all of this, and thus there can be an increase in anxiety in an already very stressful environment.

U.S. Pat. No. 5,766,008 issued to Hughes on Jun. 16, 1998, teaches what is the standard method of inserting a dental bit into the dental handpiece. One end of the shank's superior end being luted.

U.S. Pat. No. 5,749,728 issued to Bailey on May 12, 1998, teaches the use of a disposable dental angle. He uses a latch on the cap to lock the angle together. This latch is typical of the method employed in the prior art to contain the driving and driven gears and to retain a bur that is held therein.

U.S. Pat. No. 5,718,582 issued to Quinn et al. on Feb. 17, 1998, is illustrative of a patent that has a solution for the one of the most common problem encountered in dental handpieces, especially those that reach speeds of 400,000 rpm. This problem is rotation and axial slippage within the mandrel (chuck).

None of the above inventions and patents, either singly or in combination, is seen to describe the instant invention as claimed.

SUMMARY OF THE INVENTION

Accordingly, the above problems and difficulties are obviated by the present invention which provides for a disposable contra-angle to be used in association with motorized dental handpieces.

More particularly, the present invention is comprised of four major sections: a sleeve, a neck, a head and a bur attachment. The main inventive concept of the present invention being the utilization of a gear system at a relative distance from the head. This gear ratio taking place in the sleeve section, which has the largest cross sectional area. A secondary shaft, leading from the location of the gear ratio, needs to be only a fraction of the size of the main drive shaft. This allows the neck section to be thinner, thereby allowing greater visibility for the dentist. Also, by having the gear ratio take place in the sleeve section, the heaviest portion of the contra-angle is in the handle. This will create a more balanced contra-angle, one that will be easier for the dentist to control, cause less fatigue, give better access, and it will also help to keep the hands of the dentist out of and away from the patient's mouth.

The working member of the contra-angle is a bur which differs from the prior art in that it is disposable and has a new and improved means for retention within the head of the contra-angle. The present invention allows for the bur to be either placed manually by the dentist or by the manufacturer. The manufacturer would use a luting process and the bur and contra-angle would be disposed of together. The advantage of having the dentist place the bur is that it would be possible, in cases of improved materials, for the dentist to only remove the bur and thereby reuse the contra-angle a plurality of times.

Two primary considerations in designing a contra-angle system is the retention of the bur without rotation or slippage. Also the ability of the angle to deliver true spin to the working bur. Most systems today use a manually extending latch to retain the bur within the housing. The per cost of most of the burs used today is approximately $1.00. The time required to sterilize and lubricate is far in excess of that cost. Also to brush the flutes and cross cut patterns of a bur is not economical. Therefore, it is aim of the present invention to have a disposable unit.

The present invention provides a redesign of the bur shaft and the seating area within the mandrel to provide for the disposability of the bur and/or contra-angle. The aim of the present invention is to have superior retentive characteristics. Also the majority of the parts for the contra-angle can be manufactured out of plastic materials. Most prior art burs are made from a highly polished circular rod having a flat section and a circular notch for the manual latch means. The flat surface is for rotation of the bur more so than the latch. The latch is strictly a retentive feature.

The present invention utilizes a more extensive flat slot along the longitudinal suface of the bur shaft and abuts the inner chamber of the mandrel. This extension of the flat slot will resolve the problem created by too much play between bur and cylinder.

The flat side of the bur shaft is luted to a flat surface in the chamber. This aids in retention, rotation, less wobble, less noise and greater efficiency. With the present invention, the rotation of the bur will be equal to the rotation of the mandrel, thereby causing less fatigue to the hands of the dentist,lesspressure,lessenergyexpenditure,moreefficiency, less friction, less heat and subsequently more comfort for the patient.

Although the present inventon can utilize the conventional latch retention system, their failure due to inadvertent opening due to vibration has prompted the present invention to replace the external manual latch with an internal "O" ring that is contained within a recess area of the contra-angle shell. The top end of the chamber having a circular depression about its entire circumference which corresponds to the "O" ring within the recess. Within the mandrel chamber are a plurality of semi-circular protrusions which are in a cooperating relationship to a plurality of semi-circular grooves disposed in the outer surface of the bur shaft. These "O" rings and protrusions could be metal or hard plastic. Hard plastic would have more give and allow an easier insertion of the bur. An alternate embodiment to the concentric bur shaft would be to have a shaft made in in a triangular, rectangular, hexagonal or some other non-rounded shape. This would increase the rotational retention towards the idealistic 1:1 rotation.

The present invention will provide a cover over an outer boss that in itself rotates at a variable speed. This cover would be a safety feature. It being a circular piece that would either snap into place or else have means for screwing into place. The cover would also help to maintain true spin, because it would engage part of the tapered shank of the bur, thereby serving as a deterrent against the bur being dislodged.

The present invention provides an improved design feature for protection against the bur flying out of its position within the mandrel and possibly into the patient's mouth. The bur in its functional state is pushed down with some force to engage the tooth. Although the present design is for relatively low variable speeds (15–45,000 rpm), the functional force aids in retaining the bur in its housing. With the contra-angle spinning at 30,000 rpms, if the dentist inadvertently lifts the bur up, there would be the danger of the bur spinning out into the mouth of the patient. This has been seen with latching types of contra-angles. The vibration and multi-use wear loosens the latch and because this was the only retentive feature, the bur at times would slip out of the angle.

Another embodiment in the design of the present invention is the placement of a depressible ball in the chamber wall of the mandrel. This will engage within a groove about the shaft to prevent axial movement between mandrel and bur. The spring ball will spin with the shaft in the scored section.

An important object of the present invention is to prove a contra-angle that is inexpensive to manufacture and that is totally disposable.

Another object of the present invention is to provide a contra-angle that will give the dentist greater range of visibility during the procedure and also reduce vibration to the hands.

Still another object of the present invention is to provide a gear ratio closer to the hands for greater balance, thereby causing less fatigue and stress to the hands of the dentist. The major benefit of this gear ratio is that less air will be required to drive the system. Beyond economical considerations, less air means less vibration and increased frequency of rotation at the head end of the angle, thereby less auxiliary movement (non-functional) of the bur.

An object of the invention is to impart true spin to the bur which will minimize wobbling.

Another object of the invention is to redesign the bur to make the insertion and removal of the disposable bur easier for the dentist.

Yet another object of the invention is to eliminate much of the time required to brush and sterilize burs and contra-angles.

Another object of the present invention is to increase productivity of the dental office.

And the most important object of the present invention is to prevent cross infection, whereby bacteria can be transported from patient to patient or to a member of the dental staff.

These and other objects of the present invention will become readily apparent upon further review of the following specification and drawings.

BRIEF DESCRIPTION OF THE DRAWINGS

FIG. 7a is an elevational right side view of FIG. 7.

FIG. 7b is an elevational left side view of FIG. 7.

DETAILED DESCRIPTION OF THE PREFERRED EMBODIMENT

Figure 1:
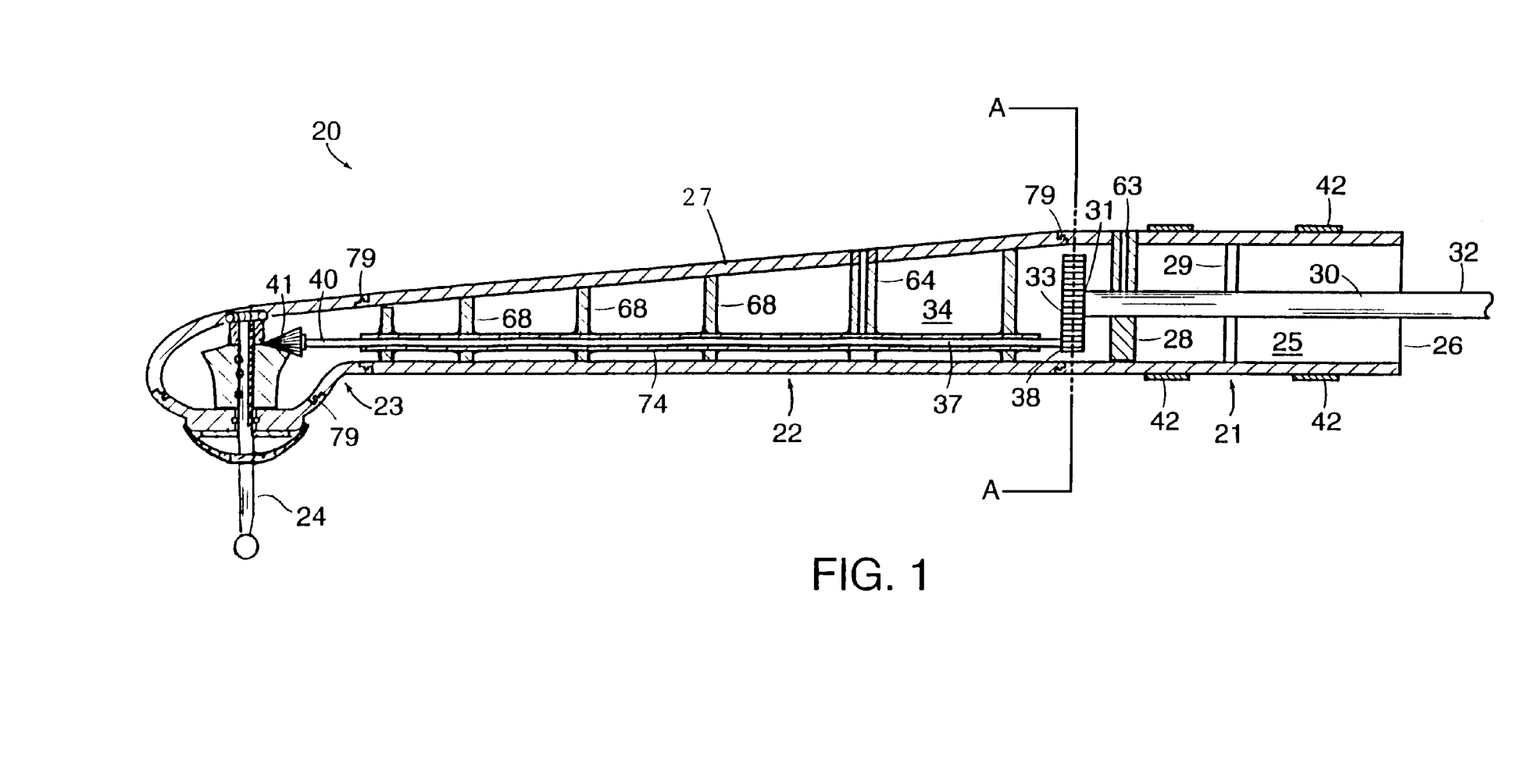
FIG. 1 is a longitudinal sectional view showing the disposable contra-angle with bur mounted therein.

Referring now to the drawings, and in particular to FIG. 1, reference numeral 20 indicates a disposable contra-angle of the present invention which is designed to operate at variable speeds (15–45,000 plus rpms). The angle 20 includes a body 27, a head section 23 and a bur member 24 that can be either removable or permanently integral within the head section 23. The body 27 includes a sleeve section 21 and a tapered neck section 22. Sleeve section 21, having means 79 for snap-fitting into neck section 22, while neck section 22 has similar means for snap-fitting into head section 23. Conventional means for connecting the sections are well known in the art. These connections can also be made by bonding the mating surfaces by suitable adhesives, fusion welding or other well known techniques. Sleeve section 21, neck section 22 and parts of the head section 23 are preferably made according to my U.S. Pat. No. 6,099,309, which was issued on Aug. 8, 2000.

Figure 2:
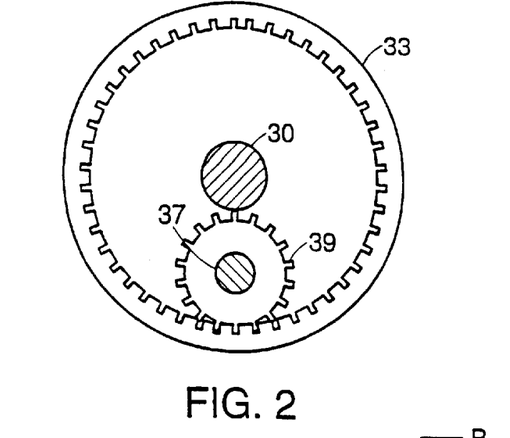
FIG. 2 is a front elevational view of the main drive gear and secondary gear taken along lines A—A of FIG. 1.

Sleeve section 21 is comprised of a thin outer shell made from a disposable plastic material, a plastic that is F.D.A. approved such as a polycarbonate resin like that marketed under the General Electric trademark LEXAN. Sleeve section 21 has a generally cylindrical elongated passageway 25 therein, and an opening 26 of sufficient diameter to accept the nose portion of a conventional dental handpiece (not shown). The handpiece is usually air or electrically driven and connected to a dental unit. The dentist can control the speed of the handpiece by pressing upon a foot pedal (rheostat). Located in close proximity to opening 26 is a standard "T" shaped keyslot (not shown) for securing the dental handpiece in place. It is presumed that this mounting means can be adapted to accept a variety of handpieces without deviating from the intent of the present invention. Integrally interposed within passageway 25 are support struts 28. Struts 28 provide stability to sleeve 21, thereby eliminating the need for a thicker shell. Each strut 28 will have an orifice 63 leading to a conduit 64, allowing the dentist/hygienist to periodicaly add dental oil for lubrication. This will be important on units designed to be used more than once and thereby requiring autoclaving, however even on disposable angles 20 it may be desired to decrease friction from time to time. An integrally interposed 360° stop 29 is positioned to orient the dental handpiece and insure that it will be properly inserted within sleeve section 21. Extending longitudinally through passageway 25 is a drive shaft 30, which has a proximal end 31 and a distal end 32. Proximal end 31 has a drive gear 33 integrally connected to it. As shown in FIG. 2, drive gear 33 has internal teeth. Distal end 32 of drive shaft 30 connects with the drive input of the dental handpiece. Struts 28 and stop 29 provide support, stabilization and alignment for drive shaft 30. Struts 28 and stop 29 being molded from the same type of plastic as sleeve section 21. Drive shaft 30 and drive gear 33 are generally made from a different grade of plastic, which is generally dependent upon the speeds of the gears and the inherent amounts of heat thereby generated. Gears usually require more flexibility and therefore a plastic such as acetal copolymer (available under the Celanese trademark CELCON) as well as many others can be used. The exterior surface of sleeve section 21 can have rubber soft pads 42 dispersed to help reduce vibration to the hands of the dentist. These pads 42 can be manufactured as part of the contra-angle 20 or else can be removably passed over sleeve section 21.

Figure 3:
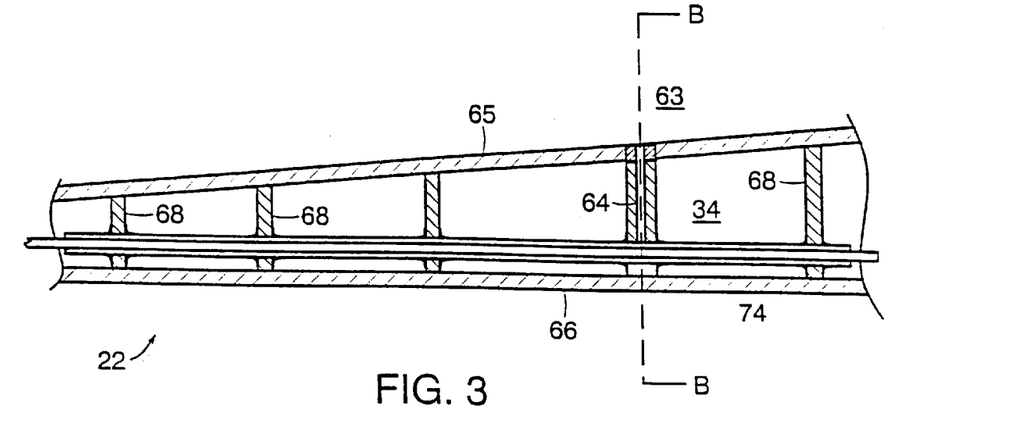
FIG. 3 is a longitudinal cross sectional view of the neck section.
Figure 4:
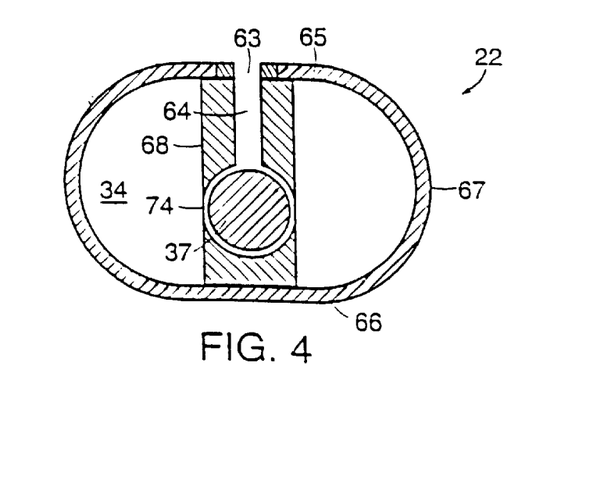
FIG. 4 is a cross sectional view of the neck section taken on lines B—B of FIG. 3.

As depicted in FIGS. 3 and 4, neck section 22 is elongated and tapered quite significantly (in respect to prior art contra-angles) and has a cross sectional shape that is flat on the top 65 and bottom 66 surfaces, while having elliptical side surfaces 67. Neck section 22 is made from the same plastic as sleeve section 21. The tapering shape allows the dentist to have greater visibility and also increases the comfort level of the patient. A circular body is also feasible with slight modification that would be known to those in the art. Neck section 22 having a bore 34 defined therein. Interposed within bore 34 are neck struts 68 which are integral with neck section 22. In addition to supporting neck section 22, they also provide support for an optional stability tube 74 which will further eliminate vibration in the system. Stability tube 74 passes longitudinally through bore 34 and provides support and alignment for a secondary shaft 37. This secondary shaft 37 moves longitudinally through tube 74 and has a first end 38 integrally connected to a secondary gear 39. Secondary gear 39 having externally mounted teeth for meshing with drive gear 33 (as shown in FIGS. 1 and 2), whereby secondary shaft 37 will have the same rotational direction as drive shaft 33. One of the inventive concepts of the present invention is in providing the gear ratio away from head section 23. Another is having on the second end 40 of secondary shaft 37 a spirally shaped driving gear 41, including gear teeth that although they gradually narrow from the outer extremity to the inner core, they also may vary in numbers and in widths and depths. The advantages of this will be stated later. Shown in the preferred embodiment but possibly eliminated for cost effective units are orifices 63, located in the neck section 22 for introducing oil which would flow through conduits 64 to lubricate the secondary shaft 37. It is to be appreciated that the slim and elongated shape of neck section 22, along with the main drive gear 33 being in the sleeve section 21, allows for a more balanced contra-angle 20, with the weight closer to the dentist's hands. This will also help to reduce stress and fatigue.

Figure 5:
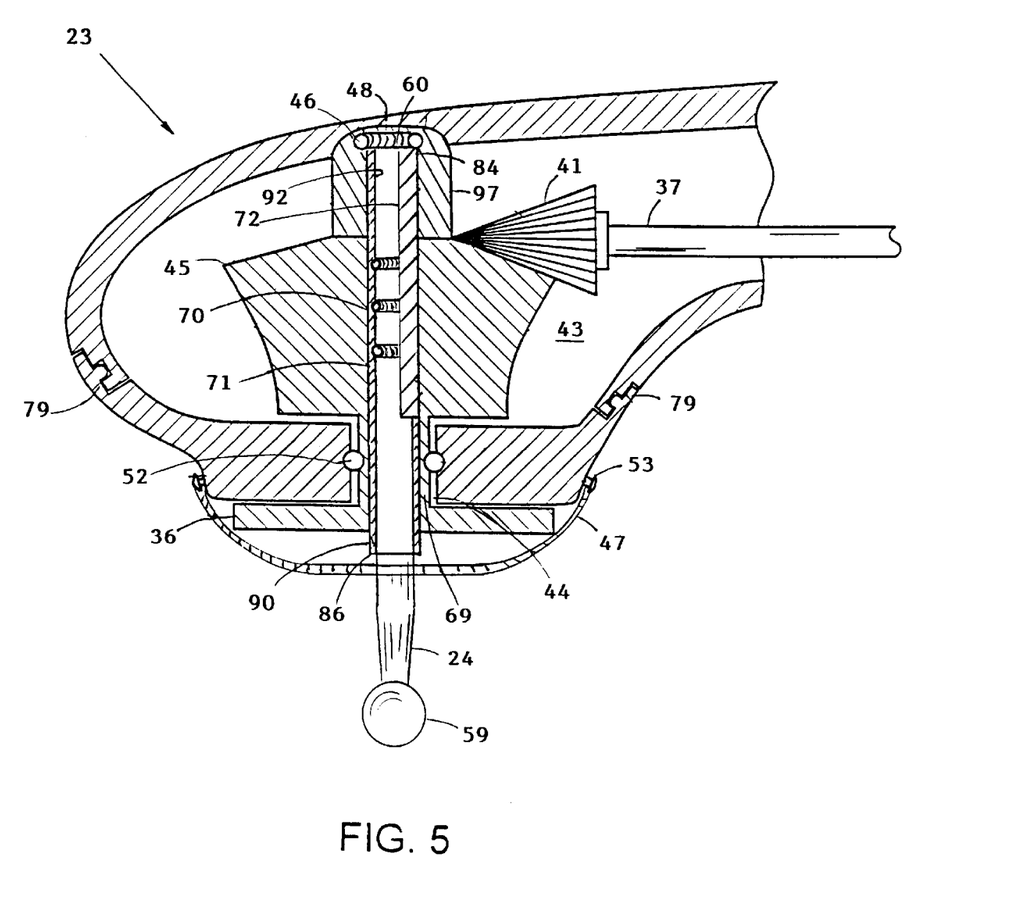
FIG. 5 is a cross sectional view of the head section and the relationship of the driving gear and the driven gear located on the mandrel.
Figure 6:
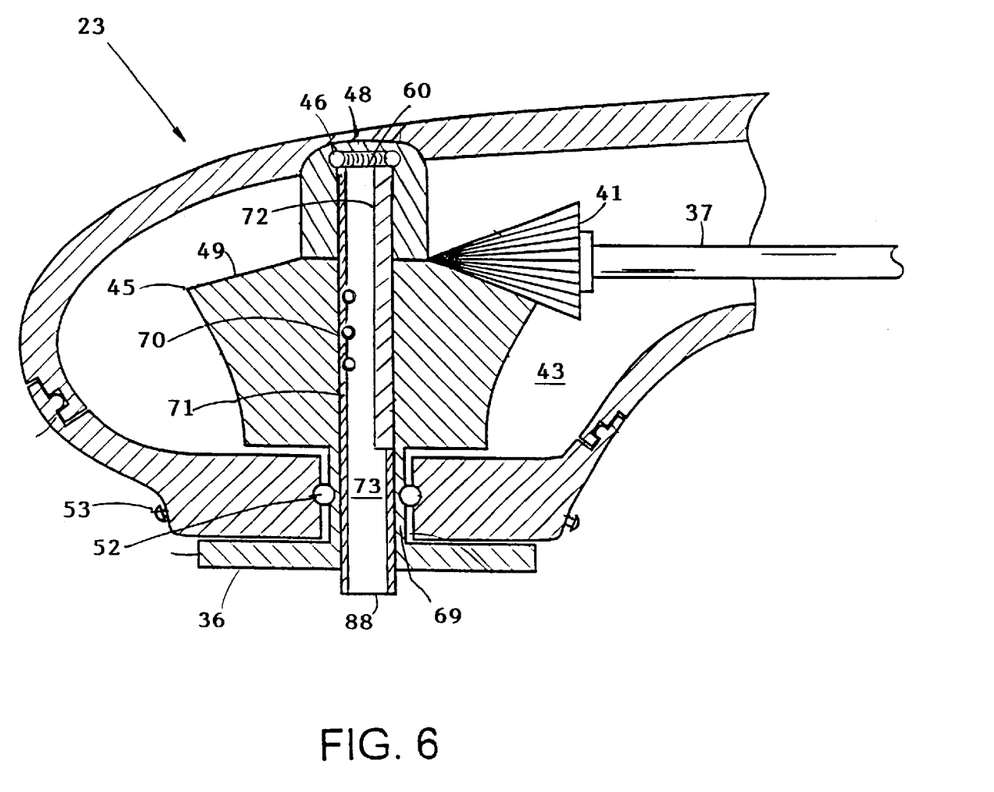
FIG. 6 is an elevational view of mandrel and chamber therein.
Figure 7:
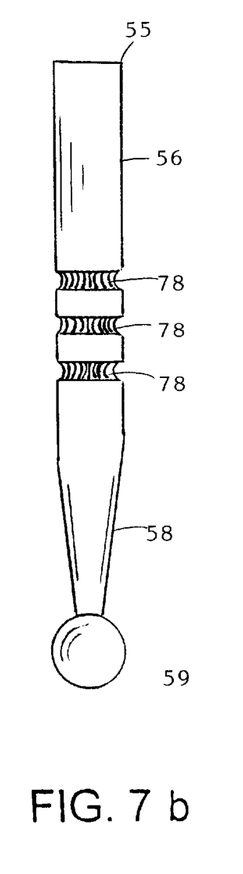
FIG. 7 ia an elevational view of the bur.
Figure 7C:
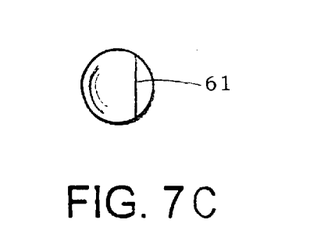
FIG. 7c is a top view of the bur.

Head section 23 and its relationship to neck section 22 and dental bur 24 are best described by FIG. 5. Head section 23 is made from the same disposable plastic as sleeve section 21. It is critical for the exterior surface of head 23 to be extremely smooth so as to eliminate possible irritations with the inner membranes of the mouth and tongue. The design of the present invention enhances this concept as rounded head 23 and neck 22 are not only smooth but smaller than conventional disposable contra-angles. Within head section 23 is a cavity 43. The bottom of head section 23 having snap-fitting means 79 to allow access. A rotating mandrel 45 is seated within cavity 43. Mandrel 45, as shown in FIGS. 6, has an elongated axis pole 71 integral with it. Axis pole 71 having a top end 84 extending from the top surface of mandrel 45 and a bottom end 86 extending downwardly from mandrel 45 through a round opening 44 defined by a wall surface 55 in the bottom portion of the head section. The outer surface 90 of axis pole 71 having a concentric shape. The inner surface 92 of axis pole 71 defining a chamber 73 therein. The chamber 73 having a flat luted surface 72 on one side. Upper outer surface 90 of axis pole 71 having a concentric depression 60 defined therein. The upper shell portion of head section 23 having a recess 48 for rotatively accepting top end 84 of axis pole 71. Insuring proper alignment and spatial positioning of mandrel 45 is a hollow cylindrical sheath 97 that extends downwardly to the upper portion of mandrel 45. Recess 48 having a circular O-Ring 46 for cooperatively mating with concentric depression 60 of axis pole 71. Axis pole 71, being integral with mandrel 45, therefore will rotate at same speed as mandrel 45. The inner surface 92 of axis pole 71 will have defined at least one semi-circular flexible protrusion 70 therein. FIG. 5 shows that the preferred embodiment has three such protrusions 70. The bottom end 86 of axis pole 71 having an aperture 88 for receiving bur member 24. Mandrel 45 having an upper surface defining spirally shaped bevel gear 49 therein. Gear 49 is put into direct engagement with driving gear 41 which is actuated by secondary shaft 37. The result being a greater contact area between gear teeth 41 and 49. The greater gear surface area means a reduction in weight, more spin and less energy expenditure. Driving gear 41 approaches driven gear 49 at a right angle but maintains a 360° groove, whereby the gears 41, 49, are locked throughout the rotation. A concentric slot portion 69 integrally connects bottom surface of mandrel 45 to a circular boss 36, while maintaining a generally parallel spatial relationship between them. Boss 36 having a diameter larger than round opening 44, thereby forms a seal with the opening 44. Slot 69 is in a friction fit with the perimeter of round opening 44. The present invention is designed to eliminate harmful vibration. Embedded in the wall surface 55 are a plurality of ball bearings 52 dispersed therein for enhancing frictionless spin. Heat, caused by friction, when combined with vibration is a major factor of wobbling. Disposed on the lower outer surface of head section 23 are snap-fitting means 53. With boss 36 rotating at the variable speeds of mandrel 45, it is imperative that boss 36 be encapsulated by a non-rotating cover 47. Cover 47 is snap-fitted onto buttons 53, however many well known means are available for connecting cover 47 to head 23, such as having threaded sections for screwing cover 47 to head 23.

FIGS. 7, 7a, 7b and 7c depict a bur member 24 of the preferred embodiment. Bur member 24 is comprised of a top shaft section 56, a tapered shank section 58, and the working end or bit 59. Bit 59 can take many shapes and forms comprising but not limited to round, inverted cone, cylindrical, oval etc. Bur member 24 of the present invention will have a flat face 61 extending along part of its length. In the manufactured units, the flat surface face 61 will juxtapose along the lute surface 72 of in chamber 73, to prevent slippage of bur 24 while it is engaged within chamber 73. To retain bur member 24 from axial movement within chamber 73, there is at least one semi-circular groove 78 defined about the exterior surface of bur 24 for meshing with flexible protrusions 70 of chamber 73. Bur member 24 can be in itself a disposable item, whereby the dentist can simply remove it for another type of bit. However, bur member 24 can also be factory installed to mandrel 45, thereby rendering the combination disposable. Factory installation would be relatively simple with all the conventional bonding agents available on the market today. Regardless of whether bur member 24 is inserted by dentist or factory installed, the elongated surface should be scored rather than highly polished. This will aid retention and reduce unwanted slippage within chamber 73.

Figure 8:
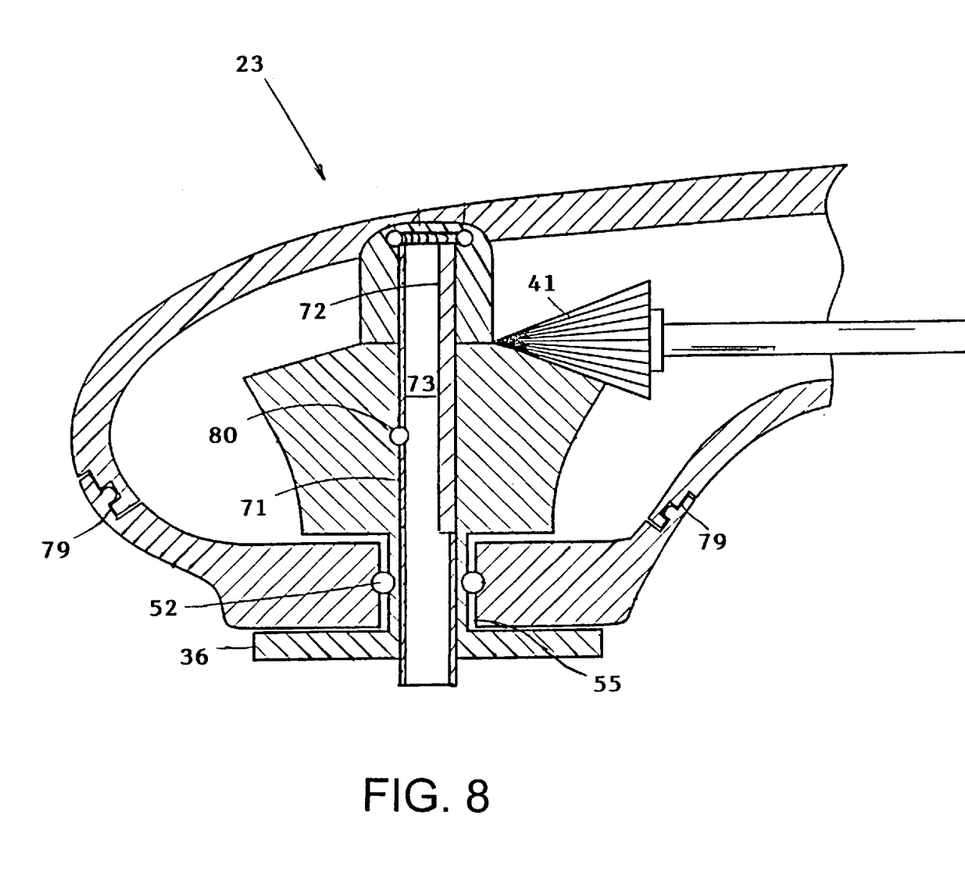
FIG. 8 is an elevational view of another embodiment having a depressed spring ball in mandrel wall.
Figure 8A:
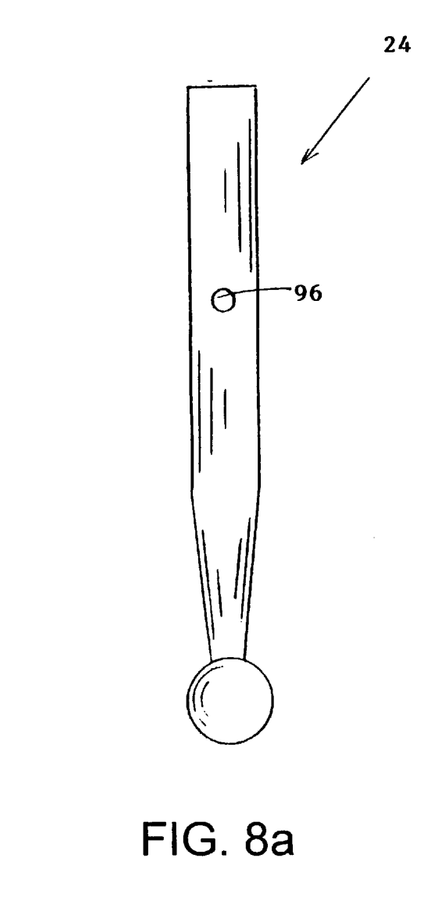
FIG. 8a is an elevational view of bur having means for cooperating with depressed spring ball of FIG. 8.

FIGS. 8 and 8a disclose another embodiment of the present invention which would provide a means for preventing axial movement of bur 24, whereby surface 92 of chamber 73 would in lieu of at least one semi-spherical protrusion 70, would have a depressed spring ball 80. Bur member 24 would then have only one semi-spherical cavity 96 to ingress ball 80.

In the embodiments of the present invention it is appreciated that the retention of bur member 24 within recess 48 can also by the conventional latching means of the prior art without deviating from the inventive concept of having disposable bur members 24 and disposable contra-angles 20.

It is illustrated above in FIGS. 1 and 2, a gear mechanism whereby a larger drive gear 33 drives a smaller secondary gear 39. However, it is to be appreciated that the present invention is not to be limited to this type of gear relationship. It is possible that under some conditions it would be more advantageous to have almost a reverse relationship, whereby a smaller gear is driving a larger gear, without deviating from the inventive concept of the invention.

It is to be understood that the present invention is not limited to the sole embodiment described above, but encompasses all embodiments within the scope of the following claims.

I claim:

1. A disposable contra-angle comprising:
    a body having one end connected to a motorized dental handpiece;
    a head section attached to the other end of the body;
    a bur member being adaptable for insertion into the head section;
    means within the body for translating rotational movement from the dental handpiece to the head section;
    the head section comprising:
    means within the head section for connecting to the rotational movement means within the body to translate the movement to the bur member;
    a cavity included therein,
    the bottom portion of the head having a concentric wall surface defining a round opening therein,
    the upper portion of the head section defining a recess, the recess having a depressed O-ring embedded therein,
    a rotating mandrel interposed within the cavity,
    an axis pole integral with and extending through and outwardly from the top and bottom center portions of the mandrel,
    the top of the axis pole having a concentric depression for adaptation to the O-ring for rotational connection and support within the recess,
    a cylindrical sheath extending downwardly from the recess for providing support, stabilization an d alignment of the axis pole,
    the bottom end of the axis pole having an aperture for receiving the bur member,
    the axis pole having means for releasably retaining and supporting the bur member.

2. The disposable contra-angle according to claim 1, wherein the retaining and supporting means of the bur member by the axis pole comprises:
    the axis pole having a chamber defined therein;
    a flat surface on one side of the chamber for making a luted connection with a similarly shaped surface of the bur;
    a plurality of semi-spherical protrusions in the inner surface of the axis pole; and
    a plurality of grooves defined on the shaft of the bur for cooperatingly connecting to the plurality of semi-spherical protrusions in the chamber of the axis pole.

3. The disposable contra-angle according to claim 2, wherein the means within the head section for translating the rotational movement of the body to the bur member comprises:
    the mandrel having a generally cylindrical top portion, a top surface having a spirally shaped bevel driven gear for engaging with the means for translating rotational movement from the dental handpiece.

4. The disposable contra-angle according to claim 3, wherein the mandrel comprises:
    a concentric slot portion extending downwardly from the top portion and rotationally interposed within the round opening of the head section;
    a circular boss integral with the concentric slot;
    the boss having a diameter larger than the round opening of the head, thereby forming a seal with the round opening and a lock against inadvertent drifting of the driven gear;
    a plurality of ball bearings partially embedded in the concentric wall for enhancing frictionless spin between the head and the concentric slot of the mandrel.

5. The disposable contra-angle according to claim 4, wherein the head section includes:
    a non-rotating cover over the rotating boss;
    a plurality of mushroom shaped buttons; and
    means for snap-fitting the cover onto the buttons.

6. The disposable contra-angle according to claim 5, wherein the body comprises;
    a generally elongated hollow sleeve section, the sleeve comprising:
    a passageway therein,
    one end of the sleeve connected to the motorized dental handpiece; and
    a generally tapered hollow neck section having one end connected to the other end of the sleeve section, the neck section comprising:
    a bore therein, and
    the other end of the neck section connected to the head section.

7. The disposable contra-angle according to claim 6, wherein the means within the body for translating rotational movement from the dental handpiece to the head section comprises:
- a drive shaft cointensively transversing through the passageway having a proximal end and a distal end,
- a drive gear integraly connected to the proximal end of the drive shaft; and
- a secondary shaft transversing through the bore, the secondary shaft having a first end and a second end,
- means for supporting the secondary shaft within the bore,
- a secondary gear integrally connected to the first end of the secondary shaft, the secondary gear having externally extending teeth for meshing with the drive gear, whereby the secondary shaft will have the same rotational direction as the drive shaft, and
- a spirally shaped driving gear integrally fixed to the second end of the secondary shaft for engaging with the beveled gear of the mandrel,
- whereby the bur member will be rotated within the mandrel.

8. A disposable contra-angle according to claim 2, wherein the number of semi-spherical protrusions is three.

9. The disposable contra-angle according to claim 1, wherein the retaining and supporting means of the bur by the axis pole comprises:
- the axis pole having a chamber defined therein;
- a flat interior surface on one side of the chamber surface for making a luted connection with a similarly shaped surface of the bur member;
- a depressed spring ball in the inner surface of the chamber; and
- a semi-spherical opening in the side surface of the bur member for ingressing the spring ball thereby causing the bur to be releasably connected to the rotating mandrel.

10. A disposable contra-angle according to claim 1, wherein the surface of the bur member is scored prior to insertion into the chamber of the axis pole to aid in the reduction of slippage.

* * * * *